United States Patent [19]

Ahmadzadeh

[11] Patent Number: 5,380,270

[45] Date of Patent: Jan. 10, 1995

[54] URETERAL CATHETER

[75] Inventor: Massoud Ahmadzadeh, Neuenkirchen, Germany

[73] Assignee: Willy Rusch AG, Kernen i.R., Germany

[21] Appl. No.: 805,482

[22] Filed: Dec. 9, 1991

[30] Foreign Application Priority Data

Dec. 7, 1990 [EP]  European Pat. Off. ........ 90123499.7

[51] Int. Cl.$^6$ .................. A61M 25/00; A61F 2/04
[52] U.S. Cl. .............................. 604/9; 623/12; 604/8
[58] Field of Search ............... 604/27, 30, 247, 248, 604/53, 52, 51, 264, 280, 281, 8-10; 128/768; 623/12

[56]  References Cited

U.S. PATENT DOCUMENTS

| | | | |
|---|---|---|---|
| 2,836,181 | 5/1958 | Tapp | 604/8 X |
| 4,169,464 | 10/1979 | Obrez | 128/657 |
| 4,225,979 | 10/1980 | Rey et al. | 623/12 |
| 4,256,102 | 3/1980 | Monaco | 604/280 |
| 4,593,670 | 6/1986 | Sheridan et al. | 604/281 |
| 4,738,667 | 4/1988 | Galloway | 604/281 |
| 4,756,708 | 7/1988 | Martin | 128/768 |
| 4,784,639 | 11/1988 | Patel | . |
| 4,787,882 | 11/1988 | Claren | 604/264 |
| 4,801,297 | 1/1989 | Mueller | 604/247 |
| 4,832,687 | 5/1989 | Smith, III | 604/51 |
| 4,935,017 | 6/1990 | Sylvanowicz | 604/53 |
| 4,987,895 | 1/1991 | Heimlich | 604/280 |
| 5,019,102 | 5/1991 | Hoene | 604/264 |
| 5,037,403 | 8/1991 | Garcia | 604/280 |
| 5,071,408 | 12/1991 | Ahmed | 606/108 |
| 5,112,301 | 5/1992 | Fenton, Jr. et al. | 604/30 |
| 5,146,925 | 9/1992 | Snow | 604/280 |

FOREIGN PATENT DOCUMENTS

| | | |
|---|---|---|
| 0208841 | 4/1986 | European Pat. Off. . |
| 0230040 | 12/1986 | European Pat. Off. . |
| 0363581 | 7/1989 | European Pat. Off. . |
| 1211941 | 12/1958 | France . |

Primary Examiner—David H. Willse
Attorney, Agent, or Firm—Thomas R. Vigil

[57]  ABSTRACT

An ureteral catheter has an elongated shaft and a lumen for drainage, the shaft has a first end with a pigtail and several openings therein, whereby the openings communicate with the lumen and the shaft has a second end with an open tip in the valve mechanism, wherein the open tip on the second end has an extendable folded shaft section and the shaft further comprises a retainer system within the valve mechanism and wherein the retainer system comprises a section, integral with the shaft, which is split into two half shafts, the half shafts being spaced apart from one another, in an unloaded mode, in a direction transverse to the lumen.

8 Claims, 4 Drawing Sheets

URETERAL CATHETER

The present invention relates to an ureteral catheter having an elongated shaft and a lumen for drainage, the shaft has a pigtail with several openings therein on its renal pelvis end, whereby the openings communicate with the lumen and the shaft has an open tip with a valve mechanism on its bladder end. Such an ureteral catheter is known from the DE 35 25 165 A1.

The known ureteral catheters comprise two pigtails for fixing the position of the catheter and for preventing an uncontrollable movement into the bladder or the renal pelvis. These catheters bypass the ureter and ensure a safe flow of the urine from the renal pelvis into the bladder. An increase of the liquid pressure in the bladder may cause backflow of the urine and thereby may cause an increase of pressure in the renal pelvis.

In the event of a natural contraction of the bladder and healthy and functioning ureterals the detrusor urinaire contracts with a simultaneous closing of the ureteral openings by the functionally associated musculus triagonalis, followed by a discharge of the urine. A backflow of the urine into the renal pelvis can be excluded.

The undesired incidents of the backflow and the increase of pressure can be counteracted by providing a valve in the bladder end of the known catheters. The DE 35 25 165 A1 teaches such a valve, whereby this valve is a planiform spear valve. Two extremely thin foil like sheets are linked with one another on their longitudinal edges. The mostly tapered end is pushed over the bladder end of the catheter and fixed to the wall of the shaft. The other opposite end of the sheet, said sheets being formed like a cone or a funnel and having a longitudinal weld, comprises transversally arranged edges which are not connected with one another. The bladder end of the catheter is located between the foil like sheets. The urine which flows from the bladder end of the catheter into the bladder is limited by the inner sides of the sheets and has to pass through an opening which is limited by the transverse edges of the sheets to reach the bladder. The bladder end of the catheter as well as the sheets forming a spear valve are located within the bladder, when the ureteral catheter is inserted. With an increase of the liquid pressure within the bladder (miction) the foil like sheets are pressed against each other, thereby closing the opening on the bladder end of the catheter. By doing this, the anti-backflow function of the natural ostiums uretris can be artificially maintained.

Furthermore, the DE 35 17 813 teaches an ureteral splint for being placed trans-ureterally, whereby the codal tip of the stent is positioned in the ureteral intermediately before the ostium of the bladder for avoiding a backflow. An irritation of the peristaltic with the possible consequence of an extasy of the tubular system as a result of a foreign body stimuli in the ureter cannot be excluded.

If the known ureteral catheters have a straight tip reaching into the bladder, the patients complain about pains in the loins during the miction. The mucous membrane of the bladder is exposed to heavy irritations and can also be injured by the bladder end of these ureteral catheters. There is also the danger that the free end moves into the urethra area of the bladder.

Theretofore, the present invention has the objective to develop the bladder end of the known ureteral catheters in such a way that, on the one hand, the mucous membrane of the bladder is not irritated during a miction, the bladder end of the ureteral catheter is always placed properly within the bladder, and on the other hand, a safe functioning of the known valve mechanism is ensured.

According to the present invention a solution to this objective is characterized in that the open tip on the bladder end has a bellows type shaft section.

Sections of a shaft having a spiral contour are also understood to be a highly flexible bellows type shaft section. The spiral may have sections with different gradients depending on the axial length and the depth of a fold can be different along the bellows type shaft section.

The ureteral catheter according to the present invention has the significant advantage that the end reaching into the bladder can always adjust to an altered contour of the bladder in an optimum way, because the ureteral catheter is provided with highly flexible features over the length of the bellows type shaft section. If the bellows type shaft section is exposed to a force from any direction it will immediately be pushed into a direction in which a resulting counter force is probably excluded, that means, the bellows type shaft section will always move into the remaining empty space within the bladder. Thereby, irritations of the mucous membrane of the bladder can be substantially avoided and an erosive trigone of the bladder can be prevented. At the same time the anti-backflow function of the natural ostium is artificially simulated in the best possible way, because a valve mechanism for preventing a urine backflow into the renal pelvis can be simply and safely adjusted to the bellows type shaft section.

The easily bendable shaft section is safely strengthened if the shaft is spirally covered over a certain length by a monofil. Even though the shaft is bent in the area of the bladder end, the lumen for drainage of the bladder end is always passable. The spiral may have different gradients along the shaft, that means, the single spiral turns are differently spaced from one another. By this action, the degree of flexibility of the shaft section depending on the length of the shaft can be influenced. Different depths of the folds in this shaft section have similar effects on the degree of the flexibility of the bellows type shaft section.

If the valve mechanism consists of a thin and highly flexible material which is formed like a funnel, whereby the valve mechanism is attached with its tapered part to the open tip of the bladder end and if the enlarged free side of the tapered part comprises a pressure-dependent, lock up opening, this kind of embodiment of a closing mechanism can be easily and safely attached to the bellows type shaft section. The foil like sheets, i.e. the whole valve mechanism, are not disturbed in their function, not even by the pigtail, since without an exerted force the bellows type shaft section lies against the mucous membrane of the bladder in a straight and extended way or reaches freely into the hollow organ.

If the tapered part of the funnel like section is formed as a reinforced shoulder, the valve mechanism takes over another function: the fixing of the position. Because of a stiffening of the sheets in the area of their fixing at the bellows type shaft section a movement of the ureteral catheter according to the present invention into the ureter is not possible. The shoulders prevent a withdrawal of the open tip of the bladder end and of the ureteral catheter into the ureter.

In another embodiment of the present invention the reinforced shoulders are incorporated strips made of metal and/or synthetic material.

This provides the advantage that the same materials can be used which are used for manufacturing and using the catheter according to the present invention. Spiral springs which form the shoulders can be used to reinforce the valve mechanism.

If the open tip of the bladder end comprises a lock part which is complementary to the lock part of a pusher, the ureteral catheter according to the present invention can be safely connected with a pusher and disconnected self-actingly by taking away the mandrel, as described in the DS-OS 38 31 652 A1. The lock part attached to the bladder end of the catheter according to the present invention is enclosed by the foil sheets which form the valve mechanism. They protect the lock part.

In another preferred embodiment of the present invention the shaft comprises a retainer system within the valve mechanism.

This provides the advantage that the ureteral catheter according to the present invention can only move as far into the ureter as the retainer system reaches the ostium uretris. The bellows type shaft section is then located within the ureter and the bladder end of the ureteral catheter according to the present invention can adapt to the changing contours of the bladder without a significant counterforce.

In a further embodiment of the present invention the retainer system is formed as a slotted shaft section which is spread in the non-loaded condition. By this action planiform fixing wings are created in a simple way which on one hand improve the valve mechanism in its function and thereby prevent a transluminal, vesico-renal back flow and on the other hand an undesired movement of the ureteral catheter within the ureter is safely prevented as well.

Further advantages arise from the description and the enclosed drawing. Furthermore, the above mentioned features as well as the ones described hereinafter can be used independently or in any combination according to the present invention. The mentioned embodiments have only exemplary character and are not to be understood as a complete list.

The present invention is illustrated in the drawings and is explained in more detail using the embodiments of the drawings as set forth below:

The single figures of the drawings show the subject matter of the present invention partly in a very schematical way and are not understood to be in scale. The parts of the single figures are partially illustrated very much enlarged for a better understanding of their structure.

Figure 1:
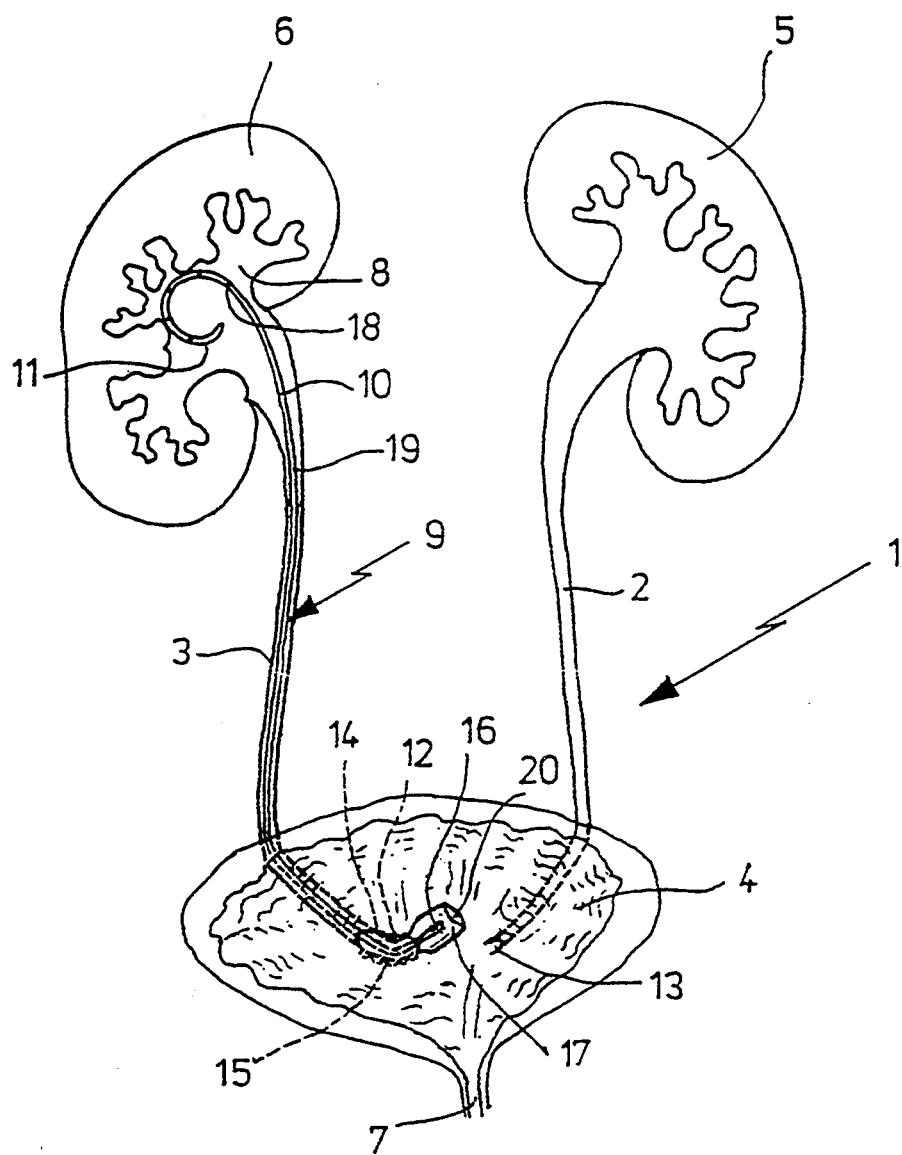
FIG. 1 shows the urogenital part of a patient having ureters, kidneys and a bladder as well as a ureteral catheter according to the present invention positioned within the right ureter.

FIG. 1 shows a sectional view of a urogenital part 1 having a left ureter 2, a right ureter 3, a bladder 4, a left kidney 5 and a right kidney 6. An urethra 7 is shown leading out of the bladder 4. A ureteral catheter 9 is positioned in the renal pelvis 8 of the right kidney 6 which leads into the right ureter 3 with its shaft 10 and which comprises a pigtail 11 for being positioned within the renal pelvis 8. A bladder end 12 of the ureteral catheter 9 reaches into the bladder 4. In this figure the left ostium uretris is indicated by 13 and the right ostium uretris is indicated by 14. Passing through the ostium uretris 14 the bladder end 12 of the ureteral catheter 9 reaches into the bladder 4, whereby a bellows type shaft section 15 projects into the bladder 4, the section 15, depending on the contour of the bladder, can be placed closely to the mucous membrane of the bladder. The bellows type shaft section 15 is connected to a lock part 16, which can be detachably connected with another lock part of a pusher. The structure and the function of the lock part 16 are already disclosed in DE-OS 38 31 652 A1. The lock part 16 is designed to ensure that the opening of the bladder end of the ureteral catheter 9 is not impaired. Furthermore, the open tip 12 of the bladder end is provided with a valve mechanism 17 which encloses the lock part 16 in a cone like manner and which comprises an openings on its free end. The ureteral catheter 9 is firmly and in a liquid tight way connected with the valve mechanism 17 in the area of the bellows type shaft section 15.

The pigtail 11 of the ureteral catheter 9 comprises openings 18 which communicate with a central lumen 19. The central lumen 19 extends over the whole length of the shaft 10 and is connected with an opening 20 of the valve mechanism 17.

Figure 2:
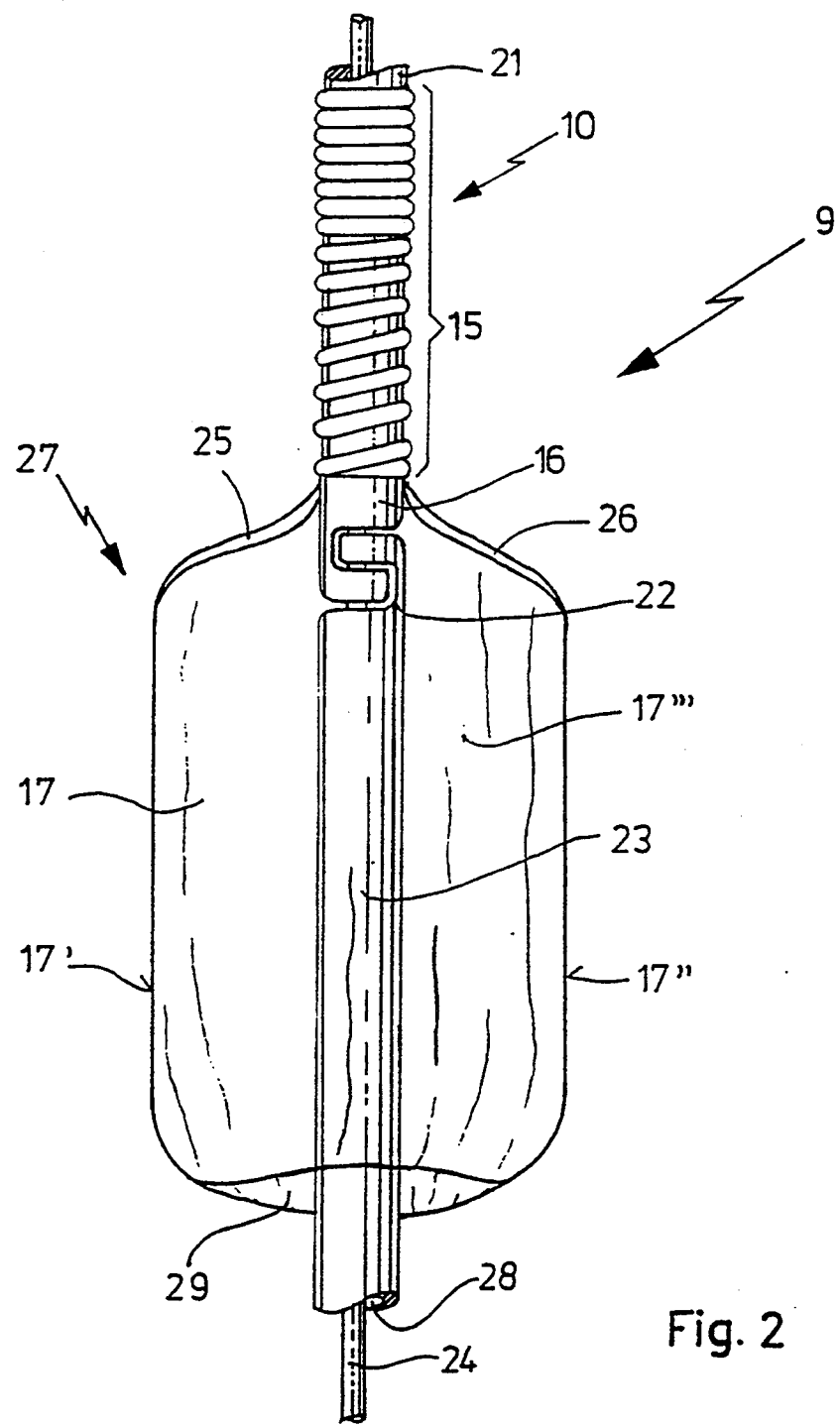
FIG. 2 shows a bladder end of a ureteral catheter according to the present invention having a pusher and a mandrel which holds together the illustrated shaft sections.

FIG. 2 shows a longitudinal section of the ureteral catheter 9 with the bladder end 12. A shaft section 21 is part of the shaft 10. The bellows type section 15 is topped by the shaft 10 on the bladder end and is form fittingly followed by the lock part 16.

On its outer surface the bellows type section 15 comprises rounded folds which line up in a knobby manner over a certain longitudinal section. The section 15 is formed by a shaft section 21 which is spirally covered by a monofil. The spiral established by the monofil comprises different gradients along the shaft section 21. The single spirals are spaced at a great distance adjacent to the valve mechanism 17, that means this part of the shaft section 21 is highly bendable into any direction. The shaft 10 is armed in this part of the shaft section 21 by the spirally covering monofil, that means the lumen for drainage remains open, even if the shaft 10 is extremely bent. Additionally, the depths of the folds in the section 15 can be influenced by differently formed monofils, that means the deeper and the more significant the folds are, the more flexible the shaft 10 is.

The embodiment of the spiral in FIG. 2 is exemplary. Furthermore, the monofil can merge with a material of the shaft.

The valve mechanism 17 is formed by a thin foil like layer made of synthetic material which has longitudinal folds 17', 17", said folds having a certain distance to the axis of the shaft, and thereby divides the encasing in a forward plane section 17''' and a backward plane section. In FIG. 2 a complementary lock part 22 engages in the lock part 16. The lock part 22 is part of a pusher 23 which can incorporate a mandrel.

The valve mechanism 17 is reinforced in the area of the bellows type shaft section 15, whereby tapering of the valve mechanism creates shoulders 25 and 26. The shoulders 25, 26 reinforce and stiffen the foil material of the valve mechanism 17 in this area. The valve mechanism 17 establishes together with the shoulders 25, 26 a retainer system 27 which prevents the bladder end of the shaft 10 from moving to the kidney side of the ureter.

The pusher 23 as well as the shaft 10 with its shaft section 21 comprise a lumen 28 for receiving the mandrel 24. The mandrel 24 keeps the lock parts 16 and 22 together. If the mandrel 24 is pulled back and the lock parts 16, 22 are uncovered, the connection opens self-actingly and the pusher 23 can be pulled off the section of the valve mechanism easily. The body liquid is led from the renal pelvis into the bladder by passing through the lumen 28.

Figure 3:
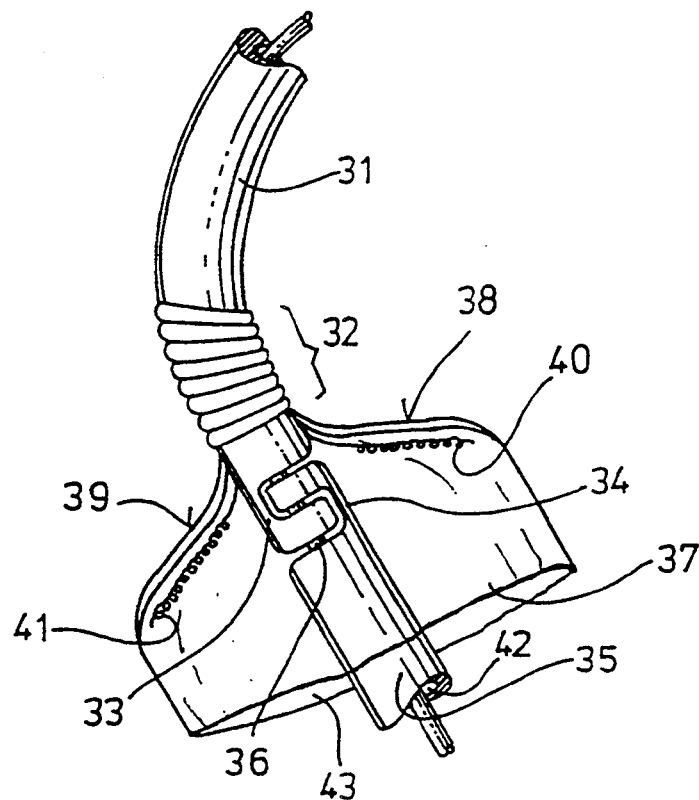
FIG. 3 shows a section of an open tip of a bladder end of a ureteral catheter according to the present invention with a shaft being bent in the area of the bellows type shaft section.

FIG. 3 shows another view of a section of a bladder end of a ureteral catheter according to the present invention. A shaft section 31 is shown in a bent manner and a bellows type shaft section 32 is jolted on one side and widened on the other side. It can be seen distinctively in FIG. 3 that the folds facilitate a bending of the shaft 31. A lock part 33 of the shaft section 31 engages in a complementary lock part 34 of a pusher 35. The lock parts 33, 34 are held together by the mandrel 36. The lock parts 33, 34 are enclosed by a valve mechanism 37 having a structure similar to the one already described. The sections of the valve mechanism 37 which are formed as shoulders 38, 39 comprise a first spiral spring 40 and a second spiral spring 41 for supporting a stiffening of these sections. The section of the mandrel 36, which is shown in FIG. 3, is guided in the lumen 42 of the pusher 35 and of the shaft section 31.

The valve mechanism 37 provides an opening 43 on its free end, said opening can be opened or closed depending on the pressure of the liquid. If some urine flows into the valve mechanism 37 passing through shaft section 31, the urine can flow into the bladder and through opening 43.

Figure 4:
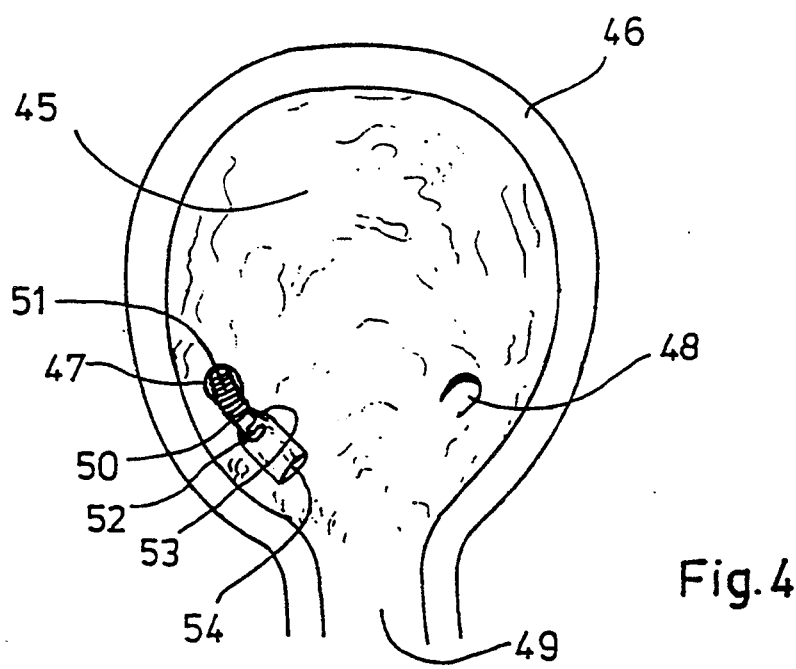
FIG. 4 shows a bladder filled with body liquid and a bladder end of a ureteral catheter according to the present invention and how it projects out of the ostium uretris.

FIG. 4 shows a sectional and highly simplified view of a bladder 45 having a musculus detrusor 46 and an ostium uretris 47 and 48. In case of a contraction of the bladder, the body liquid can be discharged by passing through ureter. A bladder end 50 of an ureteral catheter projects out of the ostium uretris 47 of the end a bellow type shaft section 51 as shown in FIG. 4. The movability of the ureteral catheter in the direction of the renal pelvis is limited by the shoulders 42, 43 of the valve mechanism. The urine can flow from the renal pelvis into the bladder 45 by passing an opening 54.

Figure 5:
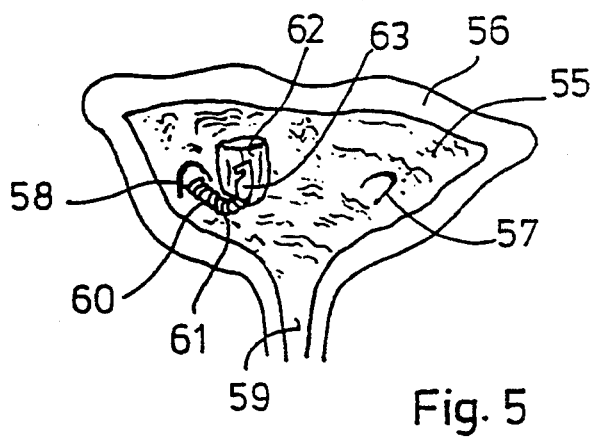
FIG. 5 shows a contracted bladder with an end of the ureteral catheter according to the present invention and how it projects out of the ostium uretris.

FIG. 5 shows a substantially emptied bladder 55 in a sectional view having an ostium uretris 57 and 58. A bladder end of the ureteral catheter 60 projects out of the ostium uretris 58 into the still remaining free space of the bladder 55. A lock part 53 which follows a bellows type shaft section 61 is enclosed by a valve mechanism 62 and, as already described, the lock parts provide an opening which has a diameter substantially as large as the diameter of the lumen of the ureteral catheter.

Figure 6:
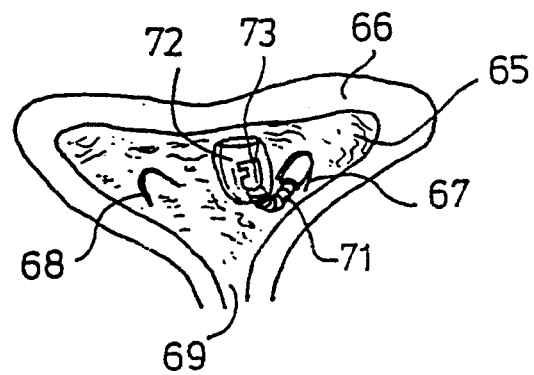
FIG. 6 shows another embodiment of a contracted bladder and how a bladder end of a ureteral catheter according to the present invention adapts to the contour of the mucous membrane the bladder.

FIG. 6 shows another embodiment of a contracted bladder 65 in a sectional view having a musculus detrusor 66 and an ostium uretris 67 and 68. The ureter is indicated by 69. A bellows type shaft section 71 lies against the mucous membrane of the bladder 65 and adjusts to the changing contours thereof. The lock part 73 is enclosed by a valve mechanism 72.

Figure 7A:
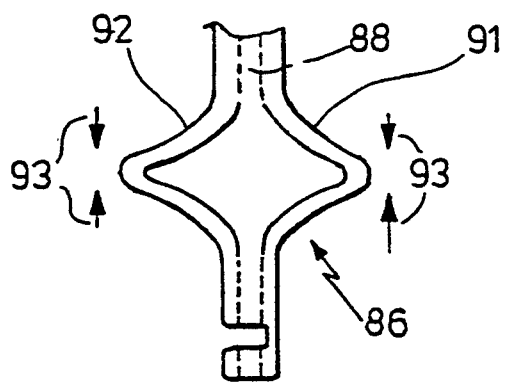
FIG. 7a shows an enlarged illustration of the retainer system of FIG. 7.
Figure 7:
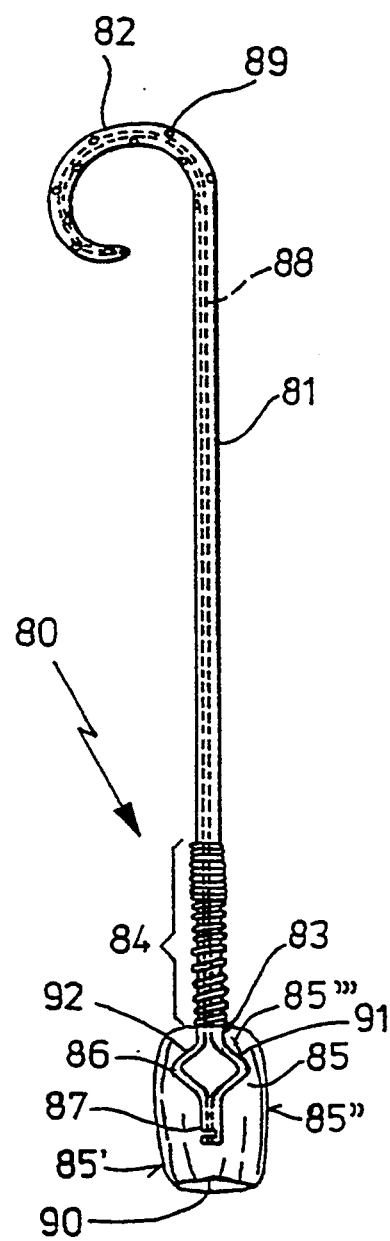
FIG. 7 shows a ureteral catheter according to the present invention having an additional retainer system within the shaft.

FIG. 7 shows an ureteral catheter 80 having a shaft 81 and a pigtail 82. At the open tip 83 of the bladder end a bellows type shaft section 84 is formed and followed by a valve mechanism 85. The valve mechanism 85 comprises a retainer system 86 which is incorporated in the shaft 81 and established by half shafts 91, 92. The retainer system 86 is enlargable to the diameter of the shaft by means of a mandrel. If the mandrel is pulled back, the shaft 81 contracts in the section of retainer system 86, thereby creating a thickening in this section (memory effect).

Additionally, the valve mechanism 85 encloses a lock part 87.

The valve mechanism 85 is formed like a hood and is welded longitudinally on its edges 85', 85" to allow a forward plane section 85''' of the hood to be pressed planiformly against a covered backward plane section in the case of an increased liquid pressure inside the bladder. The shaft 81 of the ureteral catheter 80 comprises a lumen 88 on its renal pelvis end, said lumen 88 starts at the lock part 87 and finishes at the closed renal pelvis end. The openings 89 are connected with the lumen 88. If some body liquid passes through opening 89 and reaches the lumen 88, the liquid can flow out of the ureteral catheter 80 into the bladder, thereby passing through valve mechanism 85 and opening 90.

FIG. 7a shows a retainer system 86 in an enlarged view. The valve mechanism 85 is not shown therein. The half-shafts 91, 92 are created by separating the shaft 81 in a longitudinal section in the area of the lumen 88. The half-shafts 91, 92 contract elastically in the direction of the arrows 93 (memory effect). In the contracted condition planiform positioning wings are created, which are slightly enlargable to the diameter of the shaft in directions opposite to the arrows 93 by means of a mandrel.

I claim:

1. Ureteral catheter having an elongated shaft (10; 81) and a lumen (19; 28; 42; 88) for drainage, said shaft (10; 81) having a first end with a pigtail (11; 82) and several openings (18; 89) therein, whereby said openings (18; 89) communicate with said lumen (19; 28; 42; 88) and said shaft (10; 81) having a second end with an open tip (12; 50; 60; 83) and a valve mechanism (17; 37; 62; 72; 85), wherein said open tip (12; 50; 60; 83) on the second end has an extendable folded shaft section (15; 32; 51; 61; 71; 84) and said shaft (10; 81) further comprises a retainer system (86) within said valve mechanism (17; 37; 62; 72; 85) and wherein said retainer system (86) comprises a section, integral with said shaft (10; 81), which is split into two half shafts (91, 92), said half shafts (91, 92) being spaced apart from one another, in an unloaded mode, in a direction transverse to said lumen (19; 28; 42; 88).

2. Ureteral catheter according to claim 1, wherein said shaft section (15; 32; 51; 61; 71; 84) is made of a monofil which covers spirally said shaft (10; 81).

3. Ureteral catheter according to claim 2, wherein the spiral formed by the monofil has different gradients along said shaft (10; 81).

4. Ureteral catheter according to claim 1, wherein the open tip (12; 50; 60; 83) of the second end comprises a first locking part (16; 33; 63; 73; 87) which is complementary to a second locking part (22; 34) of a pusher (23; 25).

5. Ureteral catheter having an elongated shaft (10; 81) and a lumen (19; 28; 42; 88) for drainage; said shaft (10; 81) has a first end with a pigtail (11; 82) and with several openings (18; 89) therein, whereby said openings (18; 89) communicate with said lumen (19; 28; 42; 88) and said shaft (10; 81) has a second end with an open tip (12; 50; 60; 83) and a valve mechanism (17; 37; 62; 72; 85), wherein said open tip (12; 50; 60; 83) on the second end has an extendable folded shaft section (15; 32; 51; 61; 71; 84) and said shaft further comprises a retainer system (86) within said valve mechanism (17; 37; 62; 72; 85) wherein said retainer system (86) comprises a section, integral with said shaft (10; 81), which is split into two half shafts (91, 92), said half shafts (91, 92) being spaced apart from one another, in an unloaded mode, in a direction transverse to said lumen (19; 28; 42; 88) and said valve mechanism (17; 37; 62; 72; 85) is made of a thin and highly flexible material providing a tapered part adjacent the elongated shaft (10; 81) and an enlarged part connected to said tapered part, whereby said valve mechanism (17; 37; 62; 72; 85) is attached with its tapered part to said open tip (12; 50; 60; 83) of the second end and wherein the enlarged part of the tapered part comprises a lockable opening (20; 29; 43; 54; 90), which is pressure dependent.

6. Ureteral catheter according to claim 5, wherein the tapered part of the valve-mechanism forms shoulders (25, 26; 38, 39; 52, 53) which are reinforced with material.

7. Ureteral catheter according to claim 6, wherein said reinforced shoulders (25, 26; 38, 39; 52, 53) are incorporated strips made out of at least one of metal and synthetic material.

8. Ureteral catheter according to claim 5, wherein said shaft section (15; 32; 51; 61; 71; 84) is made of a monofil which covers spirally said shaft (10; 81).

* * * * *